(12) United States Patent
Kelly

(10) Patent No.: US 11,576,497 B2
(45) Date of Patent: Feb. 14, 2023

(54) ADJUSTABLE, LOWER BACK RESTORATION DEVICE

(71) Applicant: Sean Kelly, Miami Beach, FL (US)

(72) Inventor: Sean Kelly, Miami Beach, FL (US)

( * ) Notice: Subject to any disclaimer, the term of this patent is extended or adjusted under 35 U.S.C. 154(b) by 16 days.

(21) Appl. No.: 17/066,156

(22) Filed: Oct. 8, 2020

(65) Prior Publication Data

US 2021/0106142 A1    Apr. 15, 2021

Related U.S. Application Data

(60) Provisional application No. 62/914,095, filed on Oct. 11, 2019.

(51) Int. Cl.
*A47C 20/00* (2006.01)
*A61F 5/34* (2006.01)

(52) U.S. Cl.
CPC .............. *A47C 20/021* (2013.01); *A61F 5/34* (2013.01)

(58) Field of Classification Search
CPC ................................ A47C 20/021; A61F 5/34
USPC ............................................................ 5/650
See application file for complete search history.

(56) References Cited

U.S. PATENT DOCUMENTS

| | | | | |
|---|---|---|---|---|
| 2,612,645 A | * | 10/1952 | Gus | A47C 20/048 297/DIG. 3 |
| 2,834,032 A | * | 5/1958 | Scott | A47C 20/021 5/632 |
| 2,839,766 A | * | 6/1958 | Hull | A47C 20/026 5/632 |
| 3,333,286 A | * | 8/1967 | Biolik | A47C 27/15 5/639 |
| 3,421,163 A | * | 1/1969 | Stoughton | A47C 7/425 297/452.41 |
| 3,532,336 A | * | 10/1970 | Baker | A61G 13/12 5/650 |
| 4,000,736 A | * | 1/1977 | Bruscemi | A47C 20/021 602/5 |
| 4,377,309 A | * | 3/1983 | Mengshoel | A47C 9/005 297/423.11 |
| 4,502,170 A | * | 3/1985 | Morrow | A47C 16/02 5/632 |
| 4,662,619 A | * | 5/1987 | Ray | A61G 13/12 5/624 |
| 4,685,163 A | * | 8/1987 | Quillen | A47C 20/048 5/421 |
| 4,777,678 A | * | 10/1988 | Moore | A47C 20/027 606/240 |
| 4,805,605 A | * | 2/1989 | Glassman | A61F 5/0193 128/882 |
| 4,889,109 A | * | 12/1989 | Gifford | A61G 7/0755 606/240 |
| 4,910,818 A | * | 3/1990 | Grabill | A61G 7/0755 5/494 |

(Continued)

*Primary Examiner* — David R Hare
*Assistant Examiner* — Luke Hall
(74) *Attorney, Agent, or Firm* — Nasser Ashgriz; UIPatent Inc.

(57) ABSTRACT

An adjustable lower back restoration device comprising an elevated base portion and a set of leg receiving channels divided by an upwardly upstanding central portion to position the legs of the user bent at the knees at approximately 90 degrees. The base has a height adjustment system to adjust the height of the base to the length of the upper legs of the user.

5 Claims, 22 Drawing Sheets

(56) References Cited

U.S. PATENT DOCUMENTS

| | | | | |
|---|---|---|---|---|
| 5,038,761 A * | 8/1991 | Richardson | A61F 5/0111 602/28 |
| 5,097,553 A * | 3/1992 | Boland | A61H 1/0292 5/632 |
| 5,113,875 A * | 5/1992 | Bennett | A47C 20/021 5/648 |
| 5,279,310 A * | 1/1994 | Hsien | A61F 5/01 606/240 |
| 5,289,828 A * | 3/1994 | Toth | A47C 20/021 128/DIG. 20 |
| D353,004 S * | 11/1994 | Boland | D24/183 |
| 5,432,967 A * | 7/1995 | Raftery | A47G 9/1072 D6/601 |
| 5,522,103 A * | 6/1996 | Kier | A61G 7/1009 128/845 |
| 5,718,011 A * | 2/1998 | Nogues | A47D 5/00 5/603 |
| 5,815,862 A * | 10/1998 | Rygiel | A61G 7/05769 5/733 |
| 5,871,457 A * | 2/1999 | Swedberg | A61F 5/01 606/240 |
| 5,878,453 A * | 3/1999 | Stokes | A61G 7/0755 5/648 |
| D413,981 S * | 9/1999 | Swedberg | D24/190 |
| 5,966,762 A * | 10/1999 | Wu | A61G 7/05769 5/615 |
| 6,360,387 B1 * | 3/2002 | Everhart | A47C 20/027 5/490 |
| 6,601,252 B1 * | 8/2003 | Leach | A47C 3/16 5/643 |
| 6,725,481 B1 * | 4/2004 | Marshall | A61B 6/0421 5/621 |
| 6,810,543 B2 * | 11/2004 | Fuhriman | A47C 20/021 5/632 |
| 6,935,697 B2 * | 8/2005 | Conlon | A47C 16/02 297/423.41 |
| 7,305,728 B2 * | 12/2007 | Schlieps | A47C 9/027 5/655.9 |
| 7,346,951 B1 * | 3/2008 | Heaton | A61G 7/008 5/713 |
| 8,181,295 B1 * | 5/2012 | Mallinger | A47C 20/048 5/710 |
| 8,287,439 B2 * | 10/2012 | Evans | A63B 23/0233 482/145 |
| 8,322,343 B2 * | 12/2012 | Cardin | A61G 7/0755 128/845 |
| 8,485,952 B2 * | 7/2013 | Gehrke | A47C 20/021 482/130 |
| 9,241,581 B2 * | 1/2016 | O'Nion | A47D 5/006 |
| 2004/0059268 A1 * | 3/2004 | Polonchek | A61G 7/0755 601/33 |
| 2007/0006388 A1 * | 1/2007 | Townsend | A61G 7/001 5/715 |
| 2007/0094800 A1 * | 5/2007 | Hensley | A47C 20/021 5/648 |
| 2008/0250568 A1 * | 10/2008 | Wu | A47G 9/1027 5/655.3 |
| 2011/0099851 A1 * | 5/2011 | Huber | A43B 7/142 36/140 |
| 2013/0074269 A1 * | 3/2013 | Phillips, II | A61F 5/0193 5/648 |
| 2013/0276235 A1 * | 10/2013 | Kenalty | A61G 1/0287 5/627 |
| 2015/0250326 A1 * | 9/2015 | Riccabona | A61G 7/072 5/636 |
| 2017/0360208 A1 * | 12/2017 | Kessler | A47C 20/021 |

* cited by examiner

ADJUSTABLE, LOWER BACK RESTORATION DEVICE

CROSS REFERENCE TO RELATED APPLICATION

The present invention claims priority of U.S. provisional application No. 62/914,095 entitled "Adjustable, Lower Back Restoration Pillow", filed on Oct. 11, 2019.

FIELD OF THE INVENTION

The present invention relates in general to a lower back support and in particular, to an adjustable lower back restoration device, which allows a person to comfortably elevate his or her legs while lying back or sitting.

BACKGROUND OF THE INVENTION

Chronic lower back pain is a common problem. The muscles of the lower back are tonic and almost always in a contracted state, due to the naturally extended position of the lower back and to the fact that these muscles are postural. Even when sleeping, these muscles are often contracted to some degree, depending on a person's sleeping position. Overuse and fatigue of these muscles contribute to lower back pain. Other contributing causes of lower back pain may include poor posture and poor movement patterns or injuries and strains, often attributed to overuse.

Further, when a person is lying on his or her back, stress is placed on the coccyx and sacroiliac joints and can result in sciatic nerve strain. In order to overcome this stress, a person will often lie on his or her side. However, this results in the upper leg crossing over the lower leg, placing the hips out of alignment and causing the twisting of the pelvis and spine. These may cause the rotation of the lower vertebrae, which in turn results in torsional strain on the spine and muscles of the lower back and related soft tissues. In order to overcome such problems during sleep, it is often recommended to sleep with a pillow between the knees. The pillow helps to keep the two legs and hips more even, with the legs in a more spread-apart position. This helps to reduce pelvic rotation for a more restful sleep.

Two of the only postural positions which provide relief of both chronic muscular back pain and any twisting of the lower spine, especially when a person is at rest or sleeping, are: 1) when a person is laying on his or her back but with the upper legs elevated such that they are angled at approximately 90 degrees to the upper body and, 2) when a person is laying on his or her side, in the same position and also with the legs at approximately 90 degrees, but with the knees separated such that the hips are perfectly even, in-line and straight, resulting in a perfectly straight and untwisted spine. Both positions result in the relative relaxation and neutral—neither contracted nor stretched—state of the otherwise tonic and always contracted lower back muscles. They also result in a straight, unstrained and untwisted spine. These positions are uncommon but very comfortable and often result in immediate pain relief and also a restorative and therapeutic relaxation of the lower back, gentle decompression of the lower vertebrae and spine along with all of the related muscles and connective tissues.

However, use of a conventional pillow for this purpose has proved difficult and unwieldy since any motion may act to dislodge the pillow. Further, the soft nature of many pillows does not maintain these beneficial positions. Various cushions, pillows and supports for positioning and supporting the legs/knees in a parted position have been disclosed in prior art. However, each has failed to provide a simple, yet effective positioning apparatus. Further, many do not address the issue of providing an effective position to create neutral lower back muscles. Nonetheless, this has resulted in a significant variety of products designed to try and provide greater back comfort, pain relief, health and support.

Most of these products have one fixed design. As all individuals vary anatomically, and as everyone may have a personal preference, the varying possibilities would render customization to all individuals to be impractical. Many of these inventions are made of materials that are either too hard for normal, healthy blood circulation, normal movement and adequate comfort, or too soft for adequate stability and effectiveness. One of the major issues with the current pillows that are placed between a user's legs during sleep is their inability to remain in the desired position throughout the night. As a user moves during the night, the pillow slips out from between the legs. Further, they do not address the problem of the relative position of the lower back.

The present invention provides a device to support a user in an optimal position and uniquely minimize spinal and lower back muscular stress. It is also completely customizable to fit the particular needs of each individual of any size, body and leg length. In addition, the unique design and form of the present invention provides one single solution regardless as to whether the user is lying down face up, or turns to one side or the other, or when they are in transition from one position to the others and back again. Further, the present invention also works when the user is sitting.

SUMMARY OF THE INVENTION

In one embodiment the present invention provides an adjustable leg device used to raise the user's legs such that the upper legs are oriented approximately 90° degrees upward in relation to the torso. In this position, pressure is removed from the vertebrae, bone structures, tendons and muscles in the lower back. This position is therefore relaxing and highly suitable for alleviating pain in the lower back of a user. The lower back muscles are tonic and constantly working in almost any other position. The 90-degree position of the upper leg to the torso, when the user is lying face up or to either side, generally provides the unique bodily position, whereby these muscles are neither contracted, nor flexed (stretched) but rather are in a completely relaxed and neutral state. Still, the user may elegantly self-adjust themselves by moving his/her torso slightly closer or further away from the device to engage states of slight flexion or slight extension or compete neutrality, depending on his/her lower back requirements and comfort.

In a preferred embodiment the present invention is an inflatable adjustable pillow, preferably manufactured from soft materials known in the manufacture of inflatable pillows and air mattresses, suitable for forming a device with predetermined shape. In one aspect of the present invention, the inflatable device is formed from multiple pieces of especially shaped soft flocked material sheets connected to one another, enclosing an inner space into which air can be filled via a valve.

The inflatable device has a base comprising of a plurality of portions in fluid communication with each other. The base comprises of a top portion, a bottom portion and lateral side portions elevated upwardly on both sides of the base portion. A centrally upstanding portion divides the spaces between the lateral side portions to leg receiving channels. The legs of the user are positioned on each side of the centrally upstanding portion, in the channels, with the legs bent at the knees at 90 degrees so that the knees will be positioned in a separated condition. The base has a height, which is substantially adjustable to the length of the upper legs of the user and which is adjustable to the approximate length of the user's upper leg or femur bone, such that the lower legs rest in the channels of the device horizontally.

The present invention provides inflatable layers beneath the base portion to enhance adjustment of the height of the device to approximately match the length of the user's upper leg, such that the lower legs of the user are resting at an approximately horizontal position. This facilitates manual adjustment for placing the lumbar region into a relaxed, neutral position and alleviating lower back pain. By inflating and deflating the inflatable layers, the user can adjust the device so that a comfortable, normal resting position is achieved. Air pressure to the inflatable layers is provided by the user manually or by an electric air pump or a portable electric air compressor. The electric air compressor may be remotely controlled by the user via a compressor control pad. The air compressor is powered by batteries and/or AC power.

The present invention comprises a front flap on which the user rests the weight of his lower back and torso. This unique feature elegantly utilizes the user's own body weight to help keep the device connected to the user and specifically the user's lower body. This design feature effortlessly keeps the device perfectly stable and therefore allows the user to relax all muscles of the body, especially the muscles of the legs and lower back. This feature further allows users of varying body lengths and leg lengths to benefit successfully from the relief and restoration this invention provides. Specifically, the user can simply move his or her lower back or base of their spine closer to the device, to increase the amount of degrees of the upper leg to the torso. Therefore, the user can adjust the relative extension, neutrality, or flexion of the lower back. This flap extends out on the sides than the base of the device, such that when the user turns from side to side, his/her hip will remain on the flap, holding the relative position of the user stable and in place.

In operation a user lies in the supine position on a surface with legs positioned in the leg receiving channels of the device with the knees in the desired separated position. The legs are in a position in which hips as well as knees form an angle of 90 degrees. In this position pressure is removed from vertebrae, bone structures, tendons and muscles in the lower back. This position is therefore relaxing and highly suitable for alleviating pain in the lower back of a user and the effective restoration and recuperation of the lower back following lower back strain or other injury and especially when sleeping.

The device is further usable in a seated position, when the user is sitting back with their back leaning against a vertical couch pillow, a wall, or the back board of a bed or other vertical support, instead of lying down. While the user's knees are bent to form an angle of 90 degrees between thighs and calves, more stretch and flexion is provided on all lower back muscles in this position and as desired by the user, simply by adjusting their body forward or backward on the supporting front portion or flap of the device.

The channels in the device enable the legs of the user to be placed symmetrically at a distance from each other and are long enough to keep the lower legs of the user comfortably in place. This will cause the lower back of the user to relax considerably and far more effectively. A further advantage of the channels is that the user does not have to use any muscular strength to hold the lower legs in an ideal position, since the lower legs will remain stable and supported in the channels of the device. Further, because the legs lie relaxed in the channels and even with the hips with no twisting or torque relative to the hips or each other and with the angle of the upper legs to the torso at approximately 90 degrees, the lower back and the pelvis are completely relaxed.

The device according to the invention comprises a unique shape to support the user in an ideal position. The top portion of the device is wider than the base and the soft inflated material cause the device to remain in between the legs even when the user turns from side to side during sleep. The device will follow the turns of the user during sleep or rest and will not dislodge from its position between the knees. Thus, a relaxed and optimal posture of lower back relief is maintained with the knees, upper legs and lower legs in the desired position whether the user is lying on his or her back or turning to the either side.

This invention allows for the total and complete relaxation of all the leg and torso muscles, including the hip abductor and adductor muscles—the hip muscles on the inside and outside of the legs which are completely relaxed in order for the legs of the user to drop and fall freely to the sides when the lower legs of the user are supported by the device.

In one embodiment the lateral portions of the channels extend upwardly and incline inwardly on the top portion to help prevent the legs of the user from moving off of or out of the channels.

In another embodiment of the device can be filled with memory foam or any known device fill materials, such as compressed foam, polyfill, etc. The entire device may be enclosed in an optionally stretchable device cover that creates a sense of superior tactile comfort for the user. A firm but soft foam material or flocked outer layer is used for the construction of the device to ensure the comfortable use of the device for hours at a time or for the entire night while the user is also sleeping. The softer, pliable materials allow for the adequate blood circulation of the user and therefore optimal comfort. In this embodiment, several removable and attachable layers will form the bottom of the base of the device, in order to adjust the height of the device to the approximate length of the user's femur bone or upper leg length.

In another embodiment the device has slightly rounded edges on the back and bottom portion to allow the easy turning or tipping of the device over to either side, through the user making a slight movement of the legs and hips to one side.

The inflatable device provided by the present invention has a simple structure and can be manufactured at low cost. Moreover, it can be quickly inflated for use and can be conveniently stored. It can also be conveniently transported or moved while occupying only a small fraction of the space taken up when it is fully inflated.

In another embodiment of the present invention, the lower back restoration device is made up of one "Z" shaped frame made of a solid, rigid material that will effectively support the legs of the user when the user's lower back is laying on the front portion of the "Z" shaped design. The "Z" shaped design would be covered in a soft, pliable material such as foam, or cloth or a combination of both to allow for comfort and adequate blood circulation of the user.

The "Z" shaped structure has specific angles such that the back of the user weighs down on one leg of the "Z" structure, providing stability, and the legs and feet of the user are supported by the other leg of the structure. The angles are designed to keep the user's legs such that the upper legs are oriented approximately 90° degrees upward in relation to the torso.

It is therefore an object of the present invention to provide a lower back restoration device, which keeps the lower back muscles in a neutral position, in flexion, whereby the lower back muscles are gently stretched out to varying degrees, or alternatively keeping the back in slight extension to varying degrees. This variability is important especially with respect to the unique nature of each individual lower back injury and the possible contra-indications by doctors and other health professionals of lower back flexion, or extension to optimally heal and restore the user's lower back.

It is another object of the present invention to provide a support device for the back of an individual lying on their back and additionally maintains spinal support for an individual when lying on their side in a stable position and also maintains spinal support during the transition from one position to another and back again.

It is another object of the present invention to provide an adjustable lower back support to provide a height adjustment, and possibly length adjustment which can be varied and customized to support the individual's needs based on their body type and upper and lower leg length.

It is another object of the present invention to alleviate lower back pain by relaxing or stretching out the hypertonic lower back muscles which are rarely relaxed and are often prone to overuse, strain and injury.

It is another object of the present invention to provide each individual user with a lower leg support position that is approximately horizontal. This is vital in that a position of the lower leg whereby the feet or ankle joints are higher than the knee joint which can cause an irritation to the sciatic nerve and therefore discomfort and pain to the user. Further, if the knee joints are higher than the feet or ankle joints then problems with blood circulation in the legs and subsequent discomfort may occur to some degree.

It is another object of the present invention to alleviate lower back and hip pain by keeping the legs of users comfortably in-line and even with the user's hips, such that they are not twisting their spine, whether they are lying on their back or on their side.

It is another object of the present invention to provide a lower back restoration device, which allows for portability and lightweight and compact transport, moving or shipping by the user. This is especially important given the purpose of the invention and the likelihood that the user may have a debilitating back injury to some degree or may be weaker as a result or may otherwise have pain and difficulty with movement in general.

It is another object of the present invention to provide a lower back restoration device which is soft, but firm and by its very nature and form is appropriate for a bed or other setting where users sleep and are surrounded by other soft materials and which are pliable and which are therefore easy to move or otherwise engage or disengage in use.

BRIEF DESCRIPTION OF THE DRAWINGS

Embodiments hereinafter will be described in conjunction with the appended drawings provided to illustrate and not to limit the scope of the claims, wherein like designations denote like elements, and in which:

DETAILED DESCRIPTION OF PREFERRED EMBODIMENTS

Figure 1:
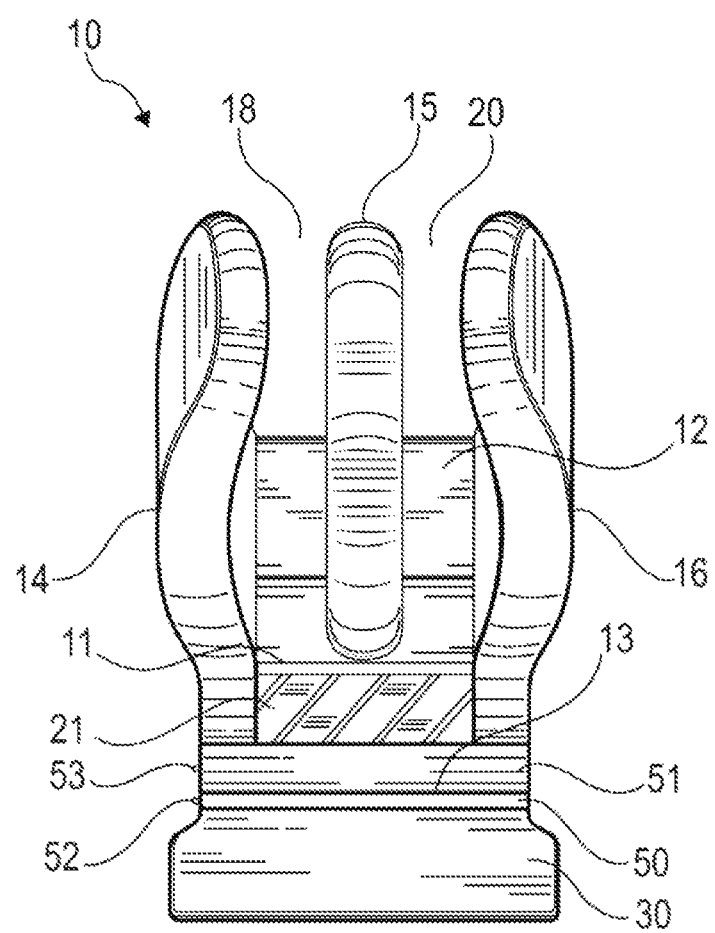
FIG. 1 is a perspective front view of the adjustable lower back restoration device of the present invention.
Figure 2:
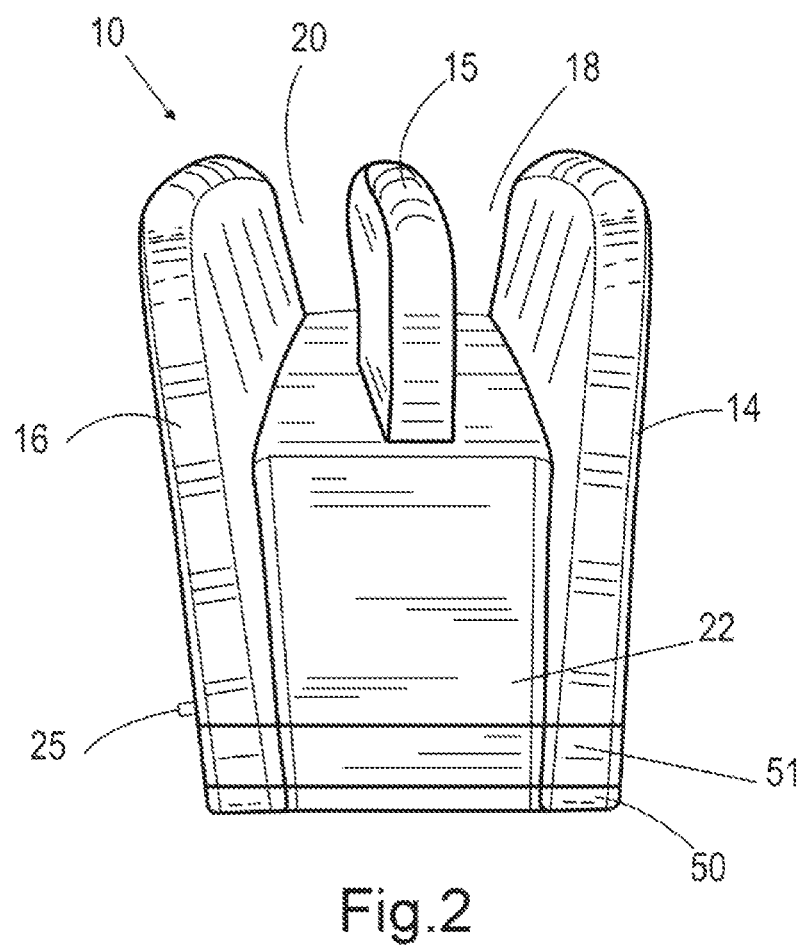
FIG. 2 is a perspective rear view of the adjustable lower back restoration device.
Figure 3:
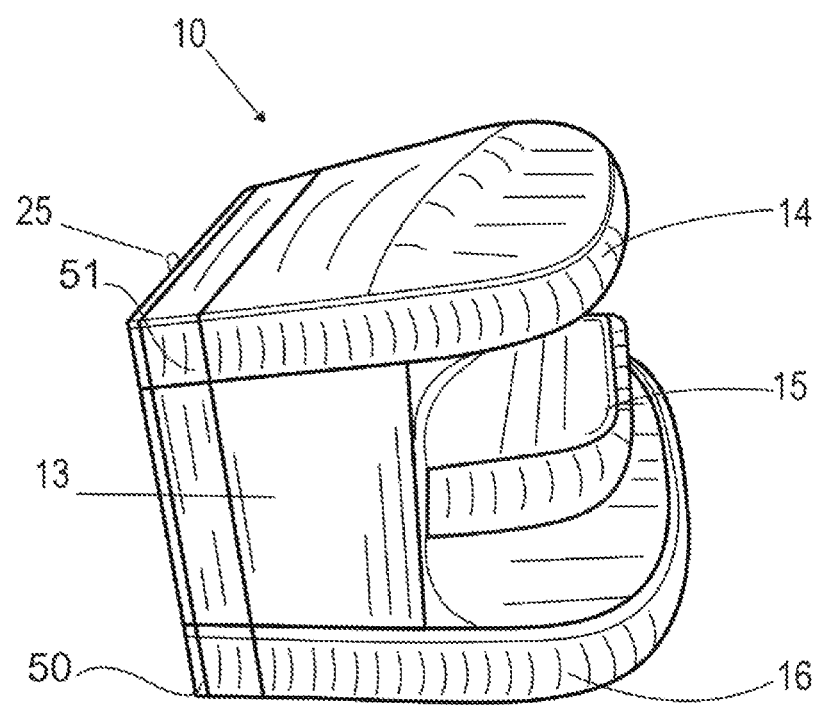
FIG. 3 is a perspective view of the bottom portion of the adjustable lower back restoration device.
Figure 4:
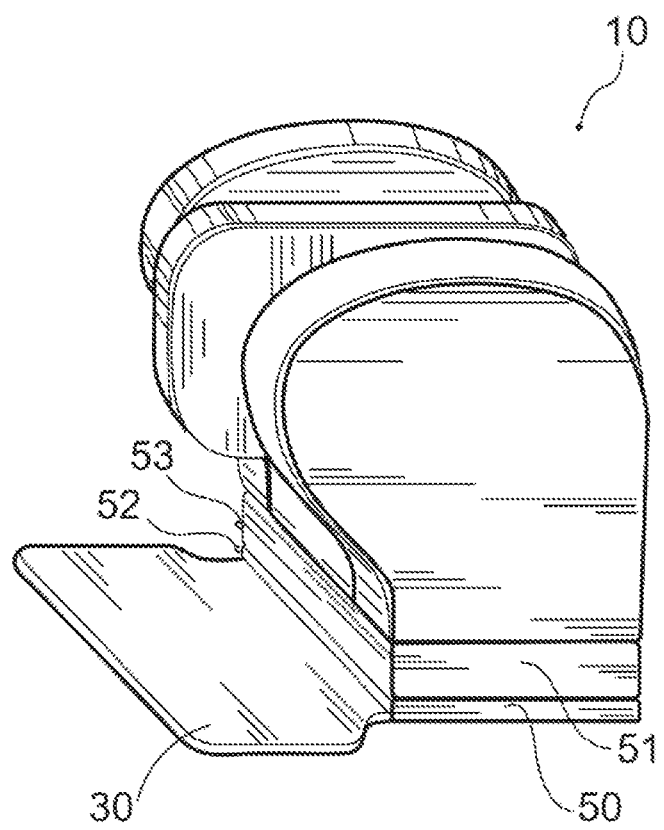
FIG. 4 is a perspective view of the present invention showing the inflatable base of the device.

A lower back restoration device 10 according to the invention is depicted in FIGS. 1 to 4. The device is a pillow 10 comprises of an inflatable structure formed from multiple pieces of soft flocked material sheets connected to one another and enclosed an inner space into which air can be filled via a valve 25.

The device 10 includes a base 11 comprising a top portion 12, a bottom portion 13, lateral side portions 14, 16, a front portion 21 and a rear portion 22. The lateral side portions 14, 16 are extended upwardly on the sides. The device 10 further has a centrally upstanding portion 15 located on the top portion 12 of the base 11 dividing the spaces between the central portion 15 and the lateral side portions 14 and 16 to leg receiving channels 18 and 20 to receive the lower legs of the user. The leg receiving channels 18, 20 extend parallel to each other in a longitudinal direction from top portion 12 and are symmetrical.

The height of the base 11 from bottom 13 to top 12 is substantially equal to the length of the upper leg of a user and is adjustable. The length of the base 11 from the front portion 21 to the back portion 22 (length of the inside of the channels) is substantially equal to the lower legs of a typical user from the knee to the ankle. The space between the lateral sides 14 and 16 is substantially equal to slightly greater than the width of the both lower legs. The length of the lateral sides 14 and 16 and the central portion 15 are long enough to prevent the legs sliding out and to keep the legs inside the channels 18 and 20. The lateral sides 14 and 16 and the centrally upstanding portion 15 have further a thickness so that the lower legs are hereby supported parallel to each other. The front portion 21 creates an angle of about 90 degrees with the channels 18 and 20. It is commonly understood that the lower back of the user can only relax completely when the upper legs are at approximately 90 degrees to the torso and are placed symmetrically, with a space between each other and when the hips remain in-line and even with each other.

The present invention 10 provides a height adjustment system to adjust the height of the base 11 with the height of all individuals to achieve the principals of the invention. The height adjustment system allows for an easy and rapid height adjustment, both in terms of increasing the height as well as decreasing the height of the device 10. A first inflatable layer 50 and a second inflatable layer 51 are shaped and sized to be provided underneath of the bottom portion 13 of the base 11. The unique design of the present invention allows for the simple adjustment of the user, by the user to create angles of the upper legs to the upper body in the range of approximately 45 to 135 degrees.

The layers 50, 51 are shaped in a manner so that the user can inflate to achieve the desired height. Each layer is provided with a valve 52 and 53 configured for adding air into the inner space of the layers. The user can control the amount of the air inserted into the layers to adjust the height of the device 10. It is to be understood that more layers can be used to further achieve the principles of the invention. The user can adjust the height of the device by inflating and deflating the layers 50 and 51. This benefits potential users from 4 feet tall to 7 feet tall. The device can vary in height from the base to the horizontal portion where the lower legs rest from, 12 inches to 21 inches. This provides parameters for the spectrum of adjustability of the inflatable base to create different appropriate heights based on femur (thigh bone) length. The layers 50 and 51 can be fabricated in various configuration.

The portions of the device 10 are in fluid communication with each other. A plurality of air-channels may be provided in the device portions 10 and layers 50, 51 to channel the air and inflate the device 10 in a specific sequence. Air inflation into the inner space of the device 10 and the inner space of the layers 50, 51 can be achieved by air pump. In one embodiment the air valves 52, 53 can be selected from air valves with levers. The inflation and deflation of the layers 50, 51 can be controlled by the lever of the air valves. In another embodiment the air pressure to the inflatable layers 50, 51 is provided by a portable electric air compressor and may be remotely controlled by the user via an air compressor control pad. The air compressor is powered by batteries, but traditional AC power is also envisioned. The user can adjust the inflatable device 10 so that the comfortable, normal resting position is achieved.

The device 10 further provides a front/flap 30 attached to the bottom portion 13. According to FIG. 4 the front flap 30 utilizes the user's own body weight to help keep the device 10 connected to the user and specifically to the user's lower body. This design feature effortlessly keeps the device 10 perfectly stable and therefore allows the user to relax all muscles of the body, especially the legs and lower back 45. Further, this front flap 30 extends out to either sides allowing the body weight of the user to transfer from the lower back to the hip, when the user turns to one side or the other. This also keeps the device 10 in place and allows the user to transition from lying flat on their back to either side and back again while maintaining the stability of the device 10 along with its effectiveness and benefits.

Figure 5A:
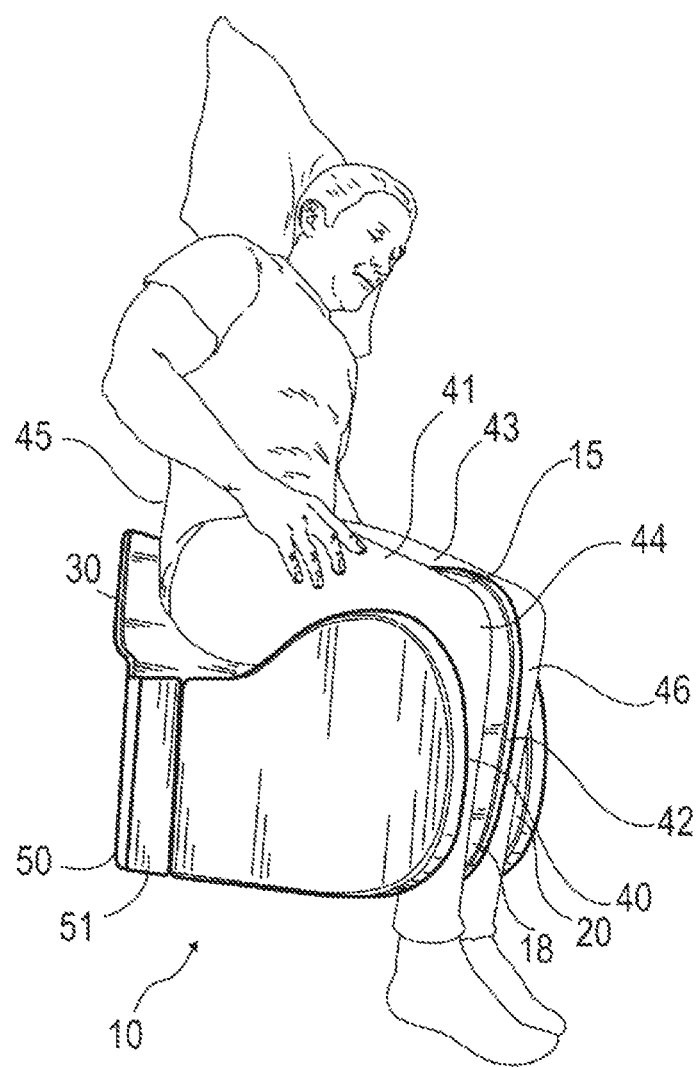
FIG. 5A is a perspective view of a user using the adjustable lower back restoration device of the invention in the supine position.
Figure 5B:
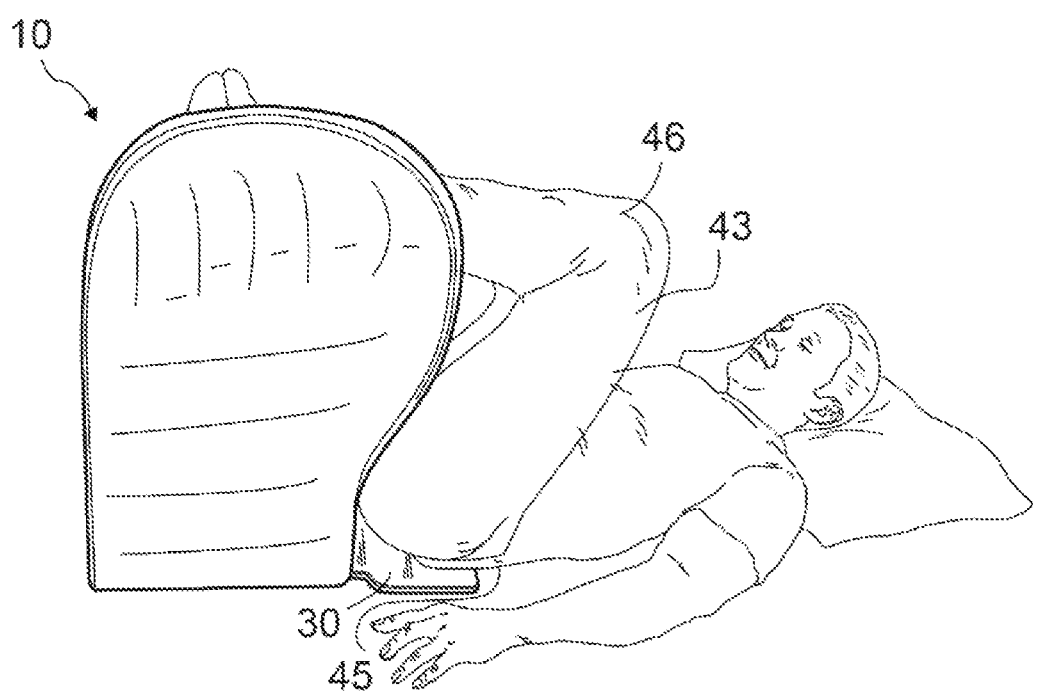
FIG. 5B is a perspective view showing a user moving forwards on the flap.
Figure 5C:
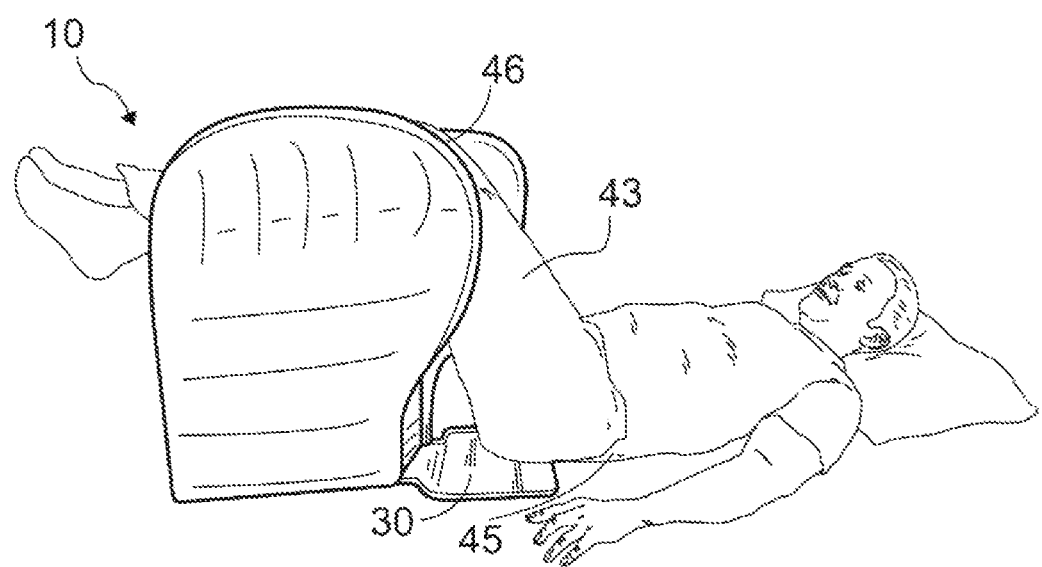
FIG. 5C is a perspective view showing the user moving backwards on the flap.
Figure 6:
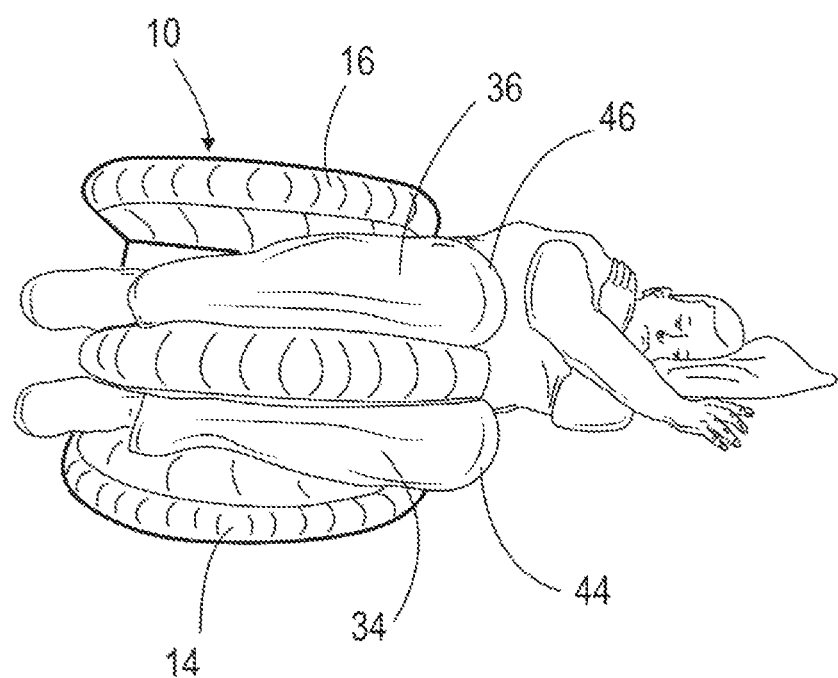
FIG. 6 is a perspective view of a user using the device of the invention in the lateral decubitus position.

The operation of the device is shown in FIGS. 5A to 6. According to FIGS. 5A, 5B and 5C a user is lying in the supine position on a surface with lower legs 40 and 42 positioned in the leg receiving channels 18 and 20 of the device with the knees 44 and 46 in the desired separated position. The legs are in a position in which the upper legs 41 and 43 form an angle of approximately 90 degrees in relation to the torso. In this position, pressure is removed from vertebrae, bone structures, tendons and muscles in the lower back 45. This position is therefore very relaxing and highly suitable for alleviating pain in the lower back 45 of the user. A higher foot compared to the knee joint can cause sciatica and related pain to the user and a lower foot than the knee may cause a lack of blood circulation in the user.

When a user is lying on a surface the lower legs 40 and 42 will tend as a result of gravitational force to sink to the deepest point of the leg receiving channels 18 and 20 while the upper legs 41 and 43 are positioned in a relation to the front portion of the base 21 creating an approximate 90 degrees angle. A further advantage of the channels 18 and 20, is that the user does not have to use any muscular strength to hold the lower legs 40 and 42 in the ideal position, since the lower legs 40, and 42 will remain laying in the channels 18 and 20 and supported in an ideal position simply due to gravitational force. This fact enhances relaxing of the lower back 45, since the legs lie even, symmetrical and relaxed in the channels 18 and 20 with the knees 43 and 44 which are folded at an angle of 90 degrees. The soft but firm sides of the device further allow the legs to drop to the sides into a state of complete muscular relaxation.

The user can move further back on the front flap 30 to decrease the number of degrees of the upper legs 41 and 43 to the lower back and spine 45. The degree variance allowed, simply from the user moving their body forward or back on the front flap 30 is approximately 45 degrees to 135 degrees. This allows for maximal comfort for each user by controlling the amount of flexion, extension, or neutrality of the lower back and spine 45 and all of the related muscles, bones, and related connective tissues.

FIG. 6 shows the device while used in the lateral decubitus position. The individual is shown lying on the left side, with the device 10 positioned between the legs. The left leg 34 rests on the left lateral portion 14. The right leg 36 is substantially on top of the left leg 34, and rests comfortably on the central portion 15 such that the legs conform to the flexed, separated position while the individual is lying on the side, preventing any twisting of the spine. The upstanding construction of the lateral sides 14, 16 and the central portion 15 prevents dislodgement of the device 10 from its position between the knees 44 and 46 of the user, even as the user turns during sleep. Each leg of the user is in contact with each corresponding channel in regardless as to whether the user turns to the left or to the right.

The front portion of the base 21 has an upward surface extending substantially vertically between top portion 12 and the bottom portion 13 with an angle of approximately 90 degrees. The front portion 21 further has an angle of approximately 90 degrees with respect to the top portion 12 and a length which is substantially equal to the length of the upper legs 41,43 of the user. The upward surface 21 is suitable for supporting the upper legs 41, 43 portions. When the user is lying on device 10, the upper legs 41, 43 will tend to move to a straightened position and exert a force against the upward surface 21 and cause to move the device to depart from the upper legs. The front flap 30 of the present invention prevent the device to depart from the user.

The lower back and the spine 45 of the user will lie on the front flap 30 to keep the device stable by effortlessly resting the user's body weight on it. This design prevents pressure of the upper legs 41 and 43 against the upward surface 21 of the device 10 from separating from the user's body via the user's own body weight. Rather, the front flap 30 actually allows the device to function effectively and with excellent stability.

The device 10 is made of soft material to enhance the natural curvatures and shape of the legs, and to create space for the user to bend the knees 44 and 46 to form an angle of 90 degrees between upper legs 41 and 43 and lower legs 40 and 42 in comfortable manner and also to allow normal blood circulation for the legs.

Figure 7:
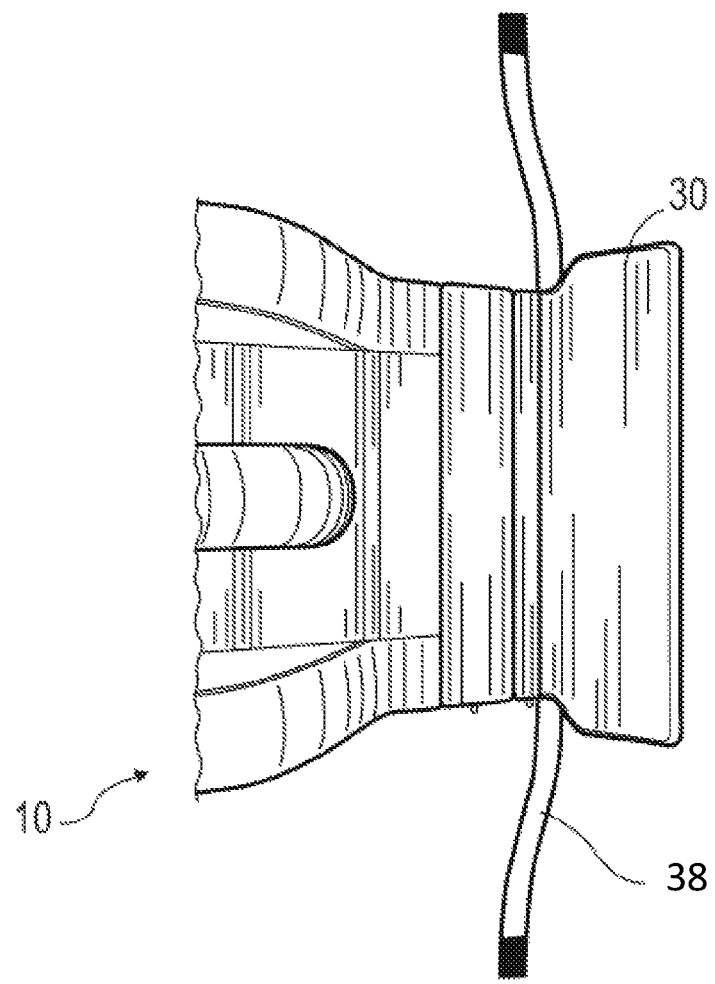
FIG. 7 is a perspective view of the present invention showing the secure belt of the device.

The device of the present invention 10 may have a securing belt. As shown in FIG. 7 a thin, 3-inch-wide, comfortable belt 38 made of soft material will attach to the bottom portion 13 by permanent attachment or removable means. The belt 38 will comfortably connect to itself across the lower abdomen area, just above the hips of the user. This adjustable belt 38 will easily attach and detach to itself also by Velcro or similar means around the user's lower abdomen and represents a feature to further comfortably and effectively secure the device 10 to the user, even when the user moves from side to side.

Figure 8A:
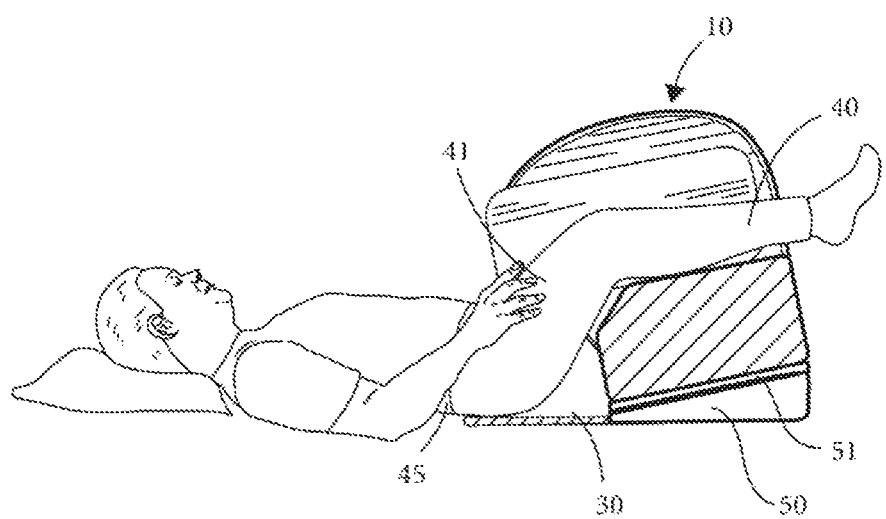
FIG. 8A is a cross sectional side view showing another embodiment of the present invention showing a user using the device in an angled position.
Figure 8B:
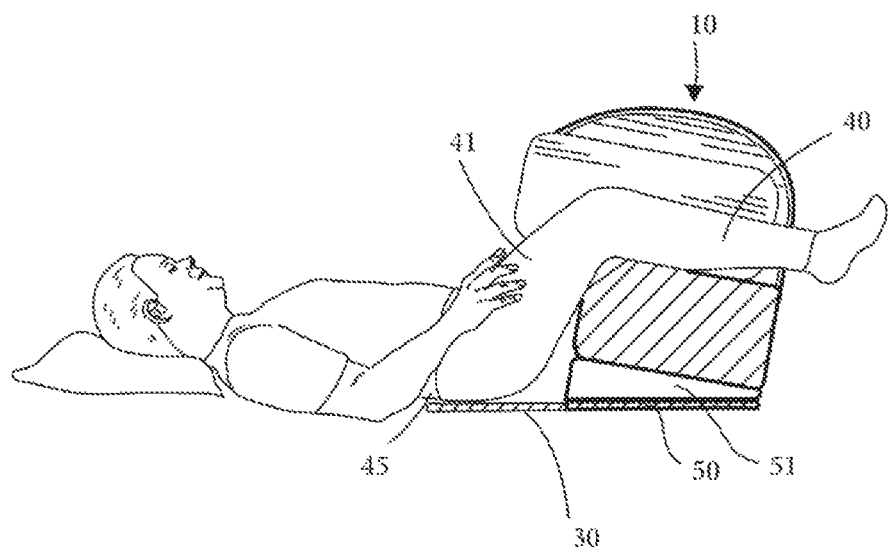
FIG. 8B is a cross sectional side view showing another embodiment of the present invention showing a user using the device in an angled position.

According to FIGS. 8A and 8B the layers can be inflated in various shapes to achieve a comfortable angle of the lower legs 40 and the upper legs 41 in relation to the lower back 45. In case, the user moves his/her body further back or forward on the front flap 30, the user can still keep the perfect angle of the legs by inflating and deflating layers 50 and 51. This design benefits to use the device 10 in different positions and allows for maximal comfort for each user by controlling the amount of flexion, extension, or neutrality of the lower back and spine 45 and all of the related muscles, bones, and related connective tissues.

Figure 9A:
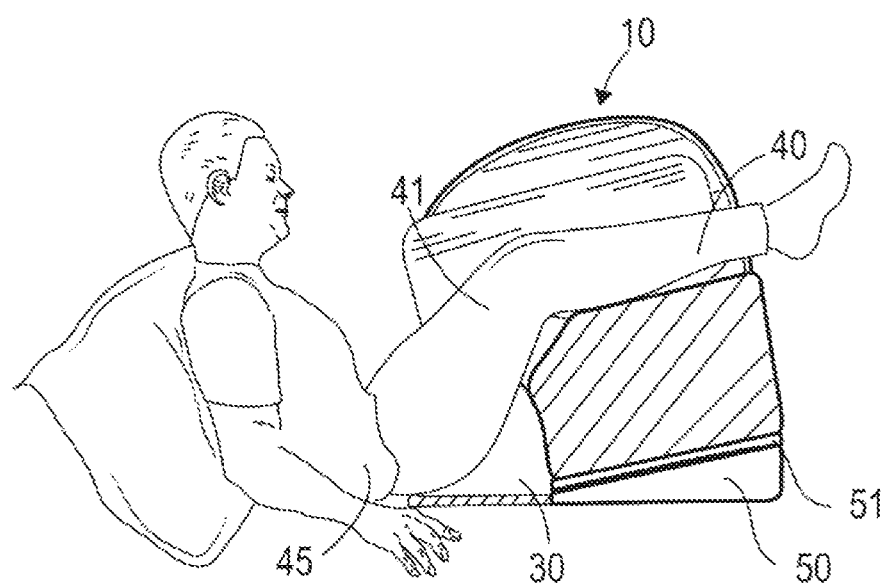
FIG. 9A is a perspective view of a user using the device of the invention in the seated position according to FIG. 8A.
Figure 9B:
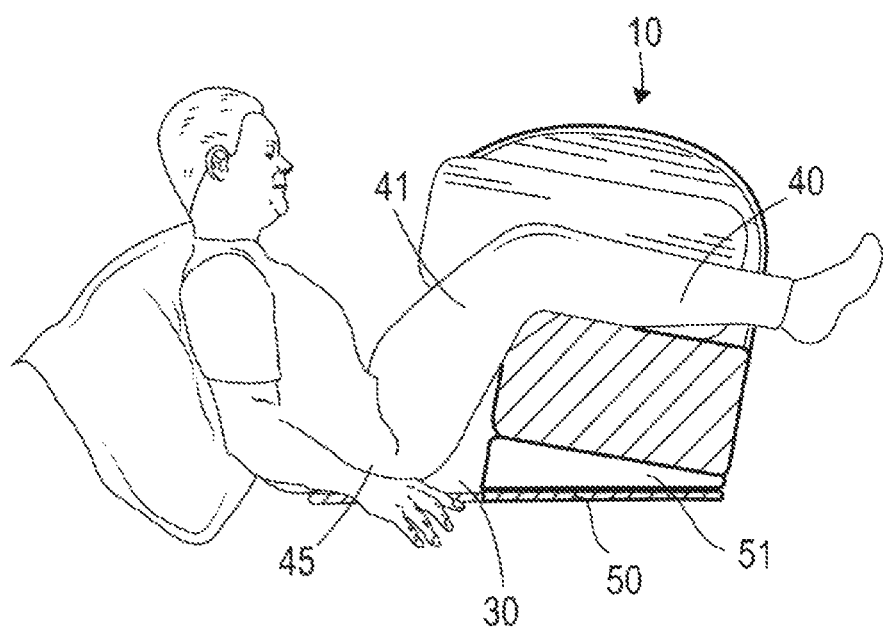
FIG. 9B is a perspective view of a user using the device of the invention in the seated position according to FIG. 8B.

FIGS. 9A and 9B show the device 10 using in a seated position while the user is sitting back in bed with his back up against a vertical couch pillow, instead of lying down with their upper body horizontal, or sitting on a typical couch while using the device 10. This seated position allows the controlled and gentle stretching out or flexing of the remainder of the back muscles while the user's knees 44 are bent to form an angle between the upper 41 and lower legs 40. The user may sit down on the non-inflated device and comfortably inflate the device to the desired height, which raises the legs, under the knees to a desired angle of hip flexion for a neutralizing or mild stretching effect on the lower back muscles 45 which is similar to the original position of using the device 10.

Figure 10A:
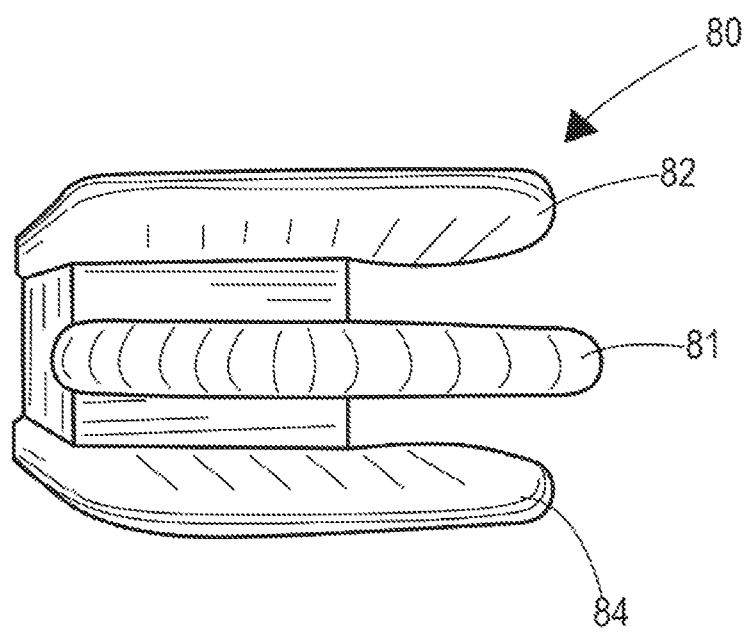
FIG. 10A is a top view of another embodiment of the present invention.
Figure 10B:
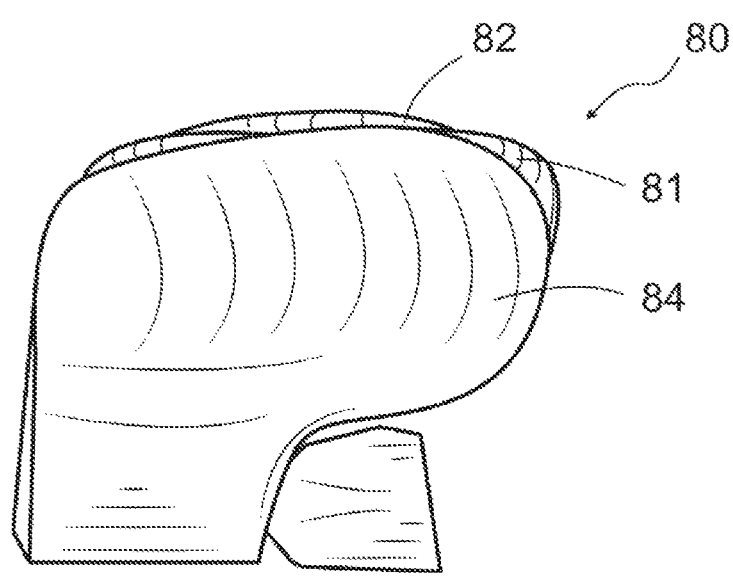
FIG. 10B is a side view of the same embodiment of the present invention according to FIG. 10A.

FIGS. 10A and 10B show another embodiment 80 of the lower back restoration device. The device 80 is made of memory foam or any known device fill materials such as compressed foam, polypill, etc. The entire device 80 may be enclosed in an optionally stretchable cover that creates a sense of superior tactile comfort for the user and that may also be removed and washed. The central portion 81 is extended forward being longer than the lateral side portions 82 and 84.

Figure 11:
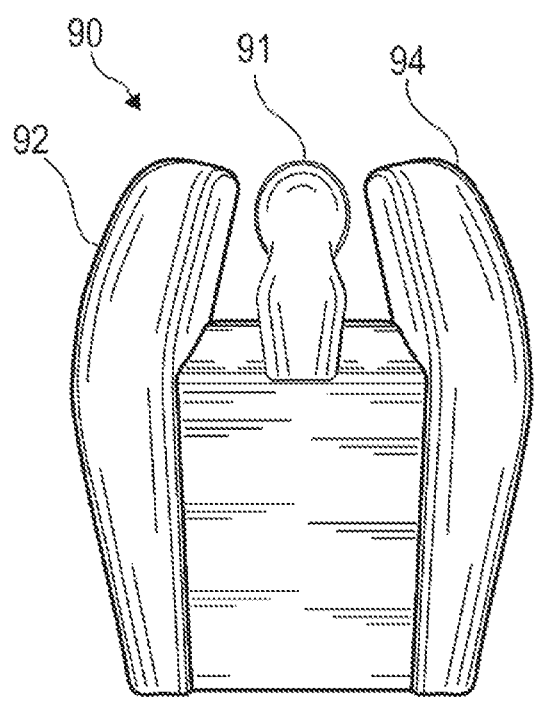
FIG. 11 is a perspective view of another embodiment of the present invention.

Referring to FIG. 11 in another embodiment 90 of the lower back restoration device the lateral sides 92 and 94 are tapered inward toward the central portion 91 to better secure the legs in position when the person turns from side to side. This provides more stability when one is laying down since the longer side portions 92 and 94 allow even people with larger lower legs to let them fall to the sides. Further, in the side position, users remain more stable since the knees are at an equal height and do not fall off the edge of the device, even when the knees are very bent.

Figure 12A:
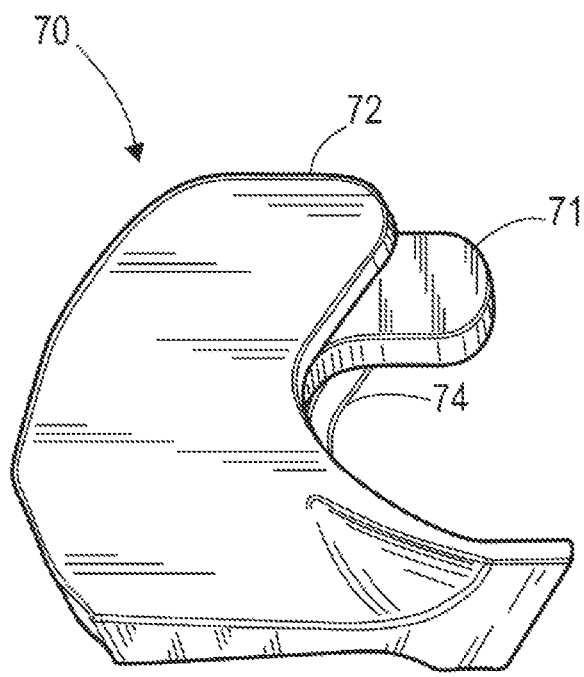
FIG. 12A is a perspective view of another embodiment of the present invention with rounded side edges.
Figure 12B:
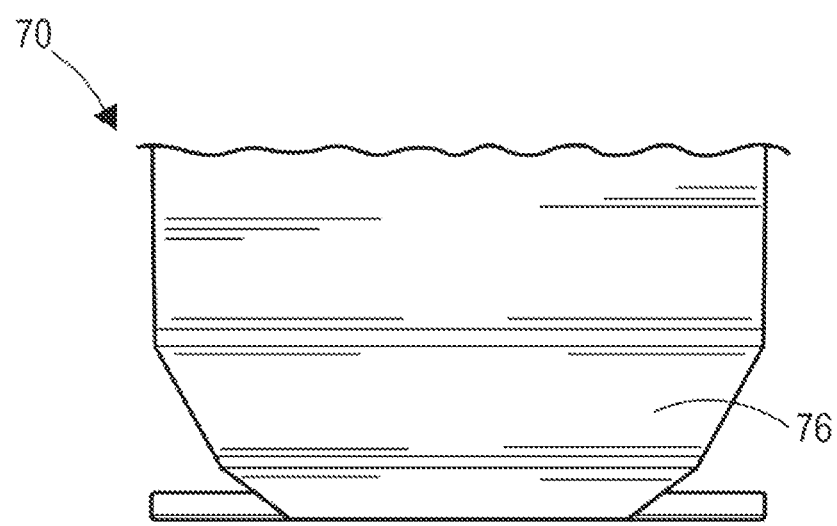
FIG. 12B is a perspective view of the present invention showing the rounded back edges according to FIG. 12A.
Figure 12C:
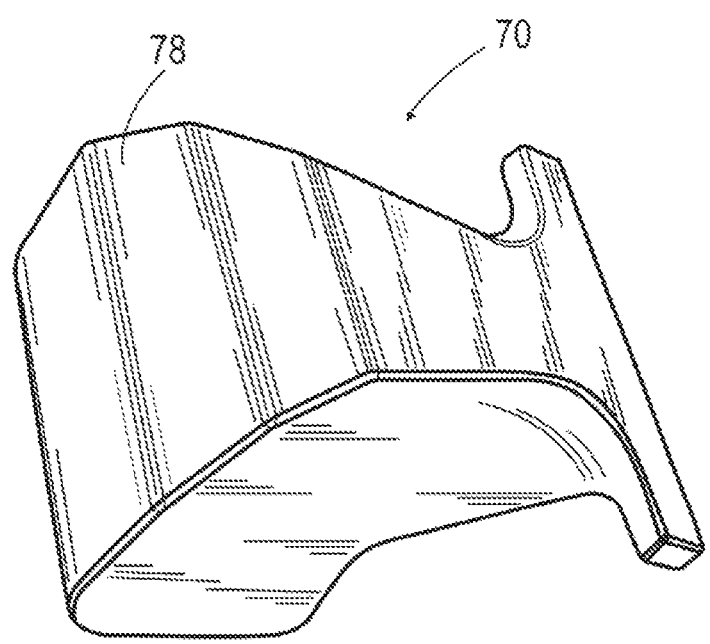
FIG. 12C is a perspective view of the present invention showing the rounded bottom edges according to FIGS. 12A and 12B.

According to FIGS. 12A, 12B and 12C in another embodiment 70 the lower back restoration device is made of memory foam or any known device fill materials such as compressed foam, polypill, etc. The foam can be cut to form rounded edges on the bottom sides 78 of the device to make it easier to tip sideways and then return to an upright position. The device 70 further may include rounded edges on the back 76 to make it easier to sit back with the device into the seated position. The central portion 71 is extended forward than the lateral side portions 72 and 74.

Figure 13A:
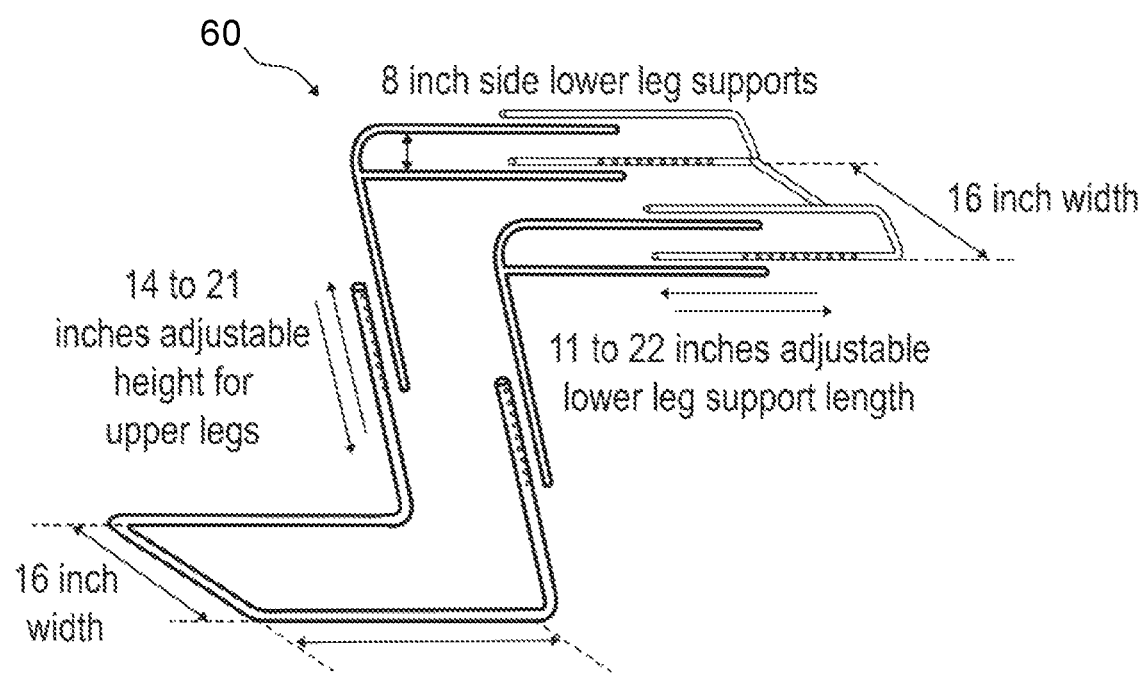
FIG. 13A is a perspective view of another embodiment of the lower back restoration device with a "Z" shaped rigid structure.
Figure 13B:
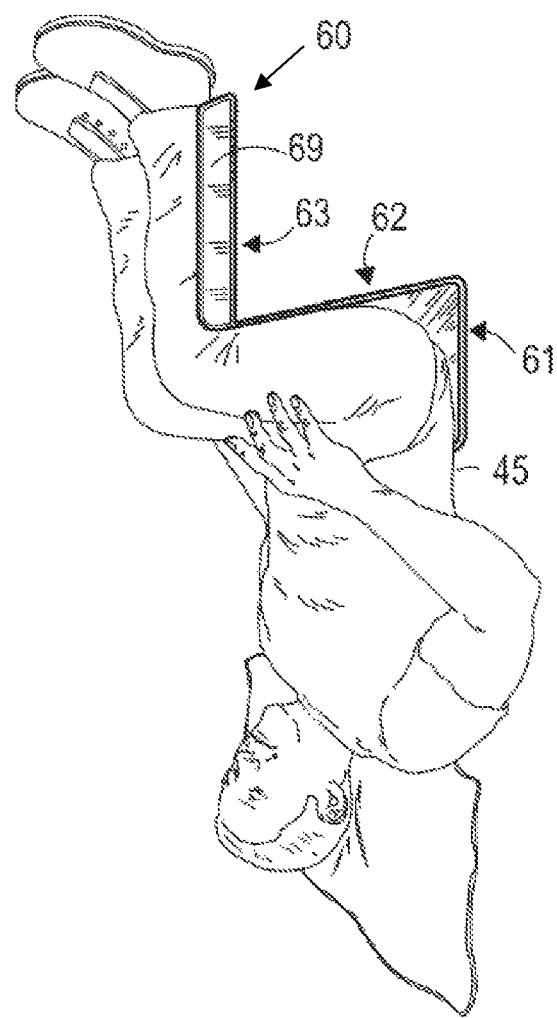
FIG. 13B is a side view showing the "Z" shaped rigid structure.
Figure 13C:
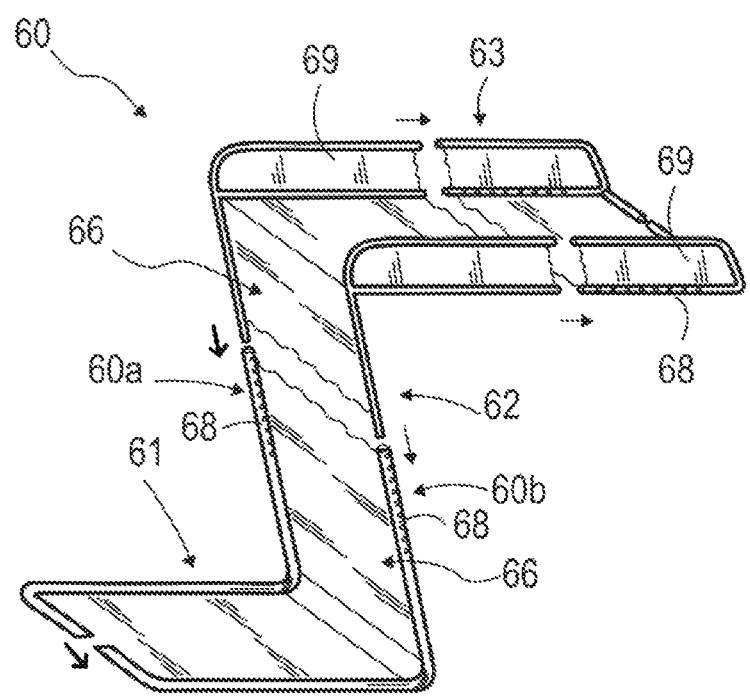
FIG. 13C illustrates the adjustable structure of the "Z" shaped rigid structure according to FIGS. 13A and 13B.

FIGS. 13A,13B and 13C show another embodiment of the present invention. The lower back restoration device is made up of a "Z" shaped frame 60 of a solid, rigid material that will effectively support the legs of the user when the user's lower back 45 is laying on the first portion of the "Z" shaped frame.

The "Z" shaped frame 60 has specific angles such that the back of the user weighs down on one leg of the "Z" structure, providing stability, and the legs and feet of the user are supported by the other leg of the structure. The angles are designed to keep the user's legs such that the upper legs are oriented approximately 90° degrees upward in relation to the torso to achieve the main aspect of the present invention.

The frame 60 comprises of two "Z" shaped side frames 60a and 60b connected to each other with a fabric or cloth 66 extending between them. The material for the frames 60a and 60b may be metal, fiberglass, plastic, wood or any other material strong enough to support the user's legs and maintain the beneficial shape of the user's legs. The rigid nature of the frames allows for the important postural position of the device, but without the thick body or thickness of the original embodiments required.

The "Z" shaped frame 60 would be covered in a soft, pliable material 66 such as foam, or cloth or a combination of both to allow for comfort and adequate blood circulation of the user. This structure forms a soft, pliable body on the middle portions. The width of the structure is about 16 inches to support the lower back, upper legs and lower legs of a user. The "Z" shaped frame 60 further comprises of a first portion 61, where the lower back of the user lies, a second portion 62, which supports the upper legs of the user, and a third portion 63 for the lower legs to rest thereon. Each of the Z-shaped side frames 60a and 60b comprise of three pieces that can be connected to each other building the sides of the frame.

[58] The base of the "Z" shaped design would be approximately 12 inches in length. The vertical portion of this embodiment would be telescopically adjustable from approximately 14 to 21 inches. The frames are telescopic tubes having connection means 68 well known in the art to adjust the height and the length of the frame 60 relative to the user's lower and upper legs length. The pieces of each part of the structure connect and slide one over the other to adjust the lengths for upper leg/femur or lower leg/tibia support. The frame 60 has a set of lower leg supporting plates 69 on the third part of the device 63 to support the lower legs in a stable position and prevent falling off from the frame.

The frame 60 is configured to adjust the height of the frame from 14 to 21 inches relative to the upper legs and similarly adjust the length of the frame forward and backward telescopically approximately from 11 to 22 inches relative to the lower legs. This structure provides for the natural statistical variances for upper legs (femur bone) and lower legs (tibia bone) lengths for people from just under 5 feet tall to approximately 7 feet tall. Two "Z" shaped side frames 60a and 60b are further removable to store the device once not in use. The relative dimensions of the various parts of the structure are shown in FIG. 13A.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. An adjustable restoration device configured to hold a lower back, lower legs, knees and upper legs of a user in a desired position, comprising:
   a) a base having a top, a bottom, a right side and a left side, a length, a front side that is configured to be towards the user and a rear side that is away from the user, and wherein the right side and the left side are upwardly extended beyond the top of the base creating a space between them and configured to receive the lower legs of the user;
   b) a central portion upwardly upstanding from the top of the base to divide the space between the right side and the left side into a right channel and a left channel, wherein the right channel is configured to receive a right leg of the user and the left channel is configured to receive a left leg of the user, wherein the right channel and the left channel have a top channel-surface, and wherein the top channel-surface has a channel-angle with respect to a front flap and a channel-height with respect to the bottom;
   c) the front flap attached to the bottom of the base and having extensions that extend beyond the right side and the left side of the base and configured to support a lower back of the user, and
   d) a height adjustment system configured to adjust the channel-height and the top channel-angle, wherein the height adjustment system comprises of a first inflatable layer that has a triangular cross section when inflated and is configured to raise the front side of the base, and a second inflatable layer that has a triangular cross section when inflated and is configured to raise the rear side of the base.

2. The device of claim 1, wherein a height of the central portion is substantially longer than the height of the right and left sides.

3. The device of claim 1, wherein the right side and the left side are tapered inward toward the central portion.

4. The device of claim 1, wherein the device has rounded edges on the right side, left side, bottom side and a back side, configured to allow for movement of the user from a supine to laying sideways, and back again.

5. The device of claim 1, wherein the device is made of memory foam, compressed foam, polyfill, or other device fill materials.

* * * * *